United States Patent [19]

Kessous-Elbaz et al.

[11] Patent Number: 5,850,001

[45] Date of Patent: *Dec. 15, 1998

[54] TRANSGENIC MOUSE FOR THE NEURONAL EXPRESSION OF HIV GP160

[75] Inventors: Allégria Kessous-Elbaz, Côte-St-Luc; Jean Michaud; Fouad Berrada, both of Montréal, all of Canada

[73] Assignee: Universite de Montreal, Montreal, Canada

[*] Notice: The term of this patent shall not extend beyond the expiration date of Pat. No. 5,569,827.

[21] Appl. No.: 685,708

[22] Filed: Jul. 24, 1996

Related U.S. Application Data

[63] Continuation-in-part of Ser. No. 254,395, Jun. 6, 1994, Pat. No. 5,569,827.

[51] Int. Cl.⁶ .............................. C12N 15/00; C07H 21/02
[52] U.S. Cl. ..................... 800/2; 435/172.3; 536/23.1; 800/DIG. 1; 800/DIG. 4
[58] Field of Search ..................................................... 800/2

[56] References Cited

U.S. PATENT DOCUMENTS 5,569,827  10/1996  Kessous-Elbaz ............................ 800/2

OTHER PUBLICATIONS

Berrada, F. et al., 1995, *J. Virol.*, 69:6770–6778.
Brenneman, D.E. et al., 1988, Nature (London), 335:639–642.
Budka, H., 1990 a), In: Chopra J, Jagannathan K, Sawhney IMS (eds) Advances in Neurology. Excerpta Medica, Amsterdam, 193–202.
Budka, H., 1990 b), Acta Neuropathol., 79:611–619.
Budka, H. et al., 1991, Brain Pathol., 1:143–152.
Cheng–Mayer, C. et al., 1987, Proc. Natl. Acad. Sci. USA, 84:3526–3530.
Dreyer, E.B. et al., 1990, Science, 248:364–367.
Epstein, L.G. et al., 1993, Ann. Neurol., 33:429–436.
Epstein, L.G. et al., 1986, Pediatrics, 78:678–687.
Gyorkey, F. et al., 1987, J. Infect. Diseases, 155:870–876.
Janssen, R.S., 1991, Neurology, 778:773–785.
Julien, J.P. et al., 1987, Genes & Development, 1:1085–1095.
Ketzler, S. et al., 1990, Acta neuropathol. (Berl), 80:92–94.
Koenig, S. et al., 1986, Science, 233:1089–1093.
Lee, M.R. et al., 1987, Science, 237:1047–1051.
Levy, J.A. et al., 1985, Lancet, ii:586–588.
Lipton, S., 1991, Brain Pathology, 1:193–199.
Lipton, S.A., 1992, Trends Neurosci., 15:76–80.
Masliah, E. et al., 1992, Lab. Investigation, 66:285–291.
Navia, B.A. et al., 1986 b), Ann. Neurol., 19:525–535.
Navia, B.A. et al., 1986 a), Ann. Neurol., 19:517–524.
Price, R.W. et al., 1988, Science, 239:586–592.
Pulliam, L. et al., 1993, AIDS Res Hum Retroviruses, 9:439–444.
Savio, T. et al., 1993, J. Neurosc. Res., 34:265–272.
Shen, Y.M. et al., 1982, Mol. Cell. Biol., 2:1145–1154.
Stoler, M.H. et al., 1986, JAMA, 256:2360–2364.
Sweetnam, P.M. et al., 1993, Eur. J. Neurosc., 5:276–283.
Vazeux, R. et al., 1987, American J. Pathol., 126:403–410.
Villa, G. et al., 1993, J Neur Neurosurgery Psy, 56:878–884.
Weis, S. et al., 1993, Acta Neuropathol., 85:185–189.
Wigdahl, B. et al., 1989, AIDS Res. Hum. Retroviruses, 5:369–374.
Wiley, C.A. et al., 1986, Proc. Natl. Acad. Sci. USA, 83:7086–7093.

*Primary Examiner*—Suzanne E. Ziska
*Attorney, Agent, or Firm*—Kevin M. Farrell

[57] ABSTRACT

The present invention relates to a transgenic non-human mammal, whose germ cells and somatic cells contain a recombinant env gene sequence which is operably linked to a promoter effective for the expression of the gene in the neuronal tissues of the mammal and effective for the simulation of neurological syndromes associated with HIV-1, the gene being introduced into the mammal, or an ancestor of the mammal, at an embryonic stage. The transgenic non-human mammal is such that transcription of the env gene may be under the control of a promoter sequence, such as a neuron specific promoter of human neurofilament heavy gene (NFH). The promoter can be synthetic or inducible. The transgenic non-human mammal can be a rodent, such as a mouse.

1 Claim, 7 Drawing Sheets

NFHgp160

KS STY T3

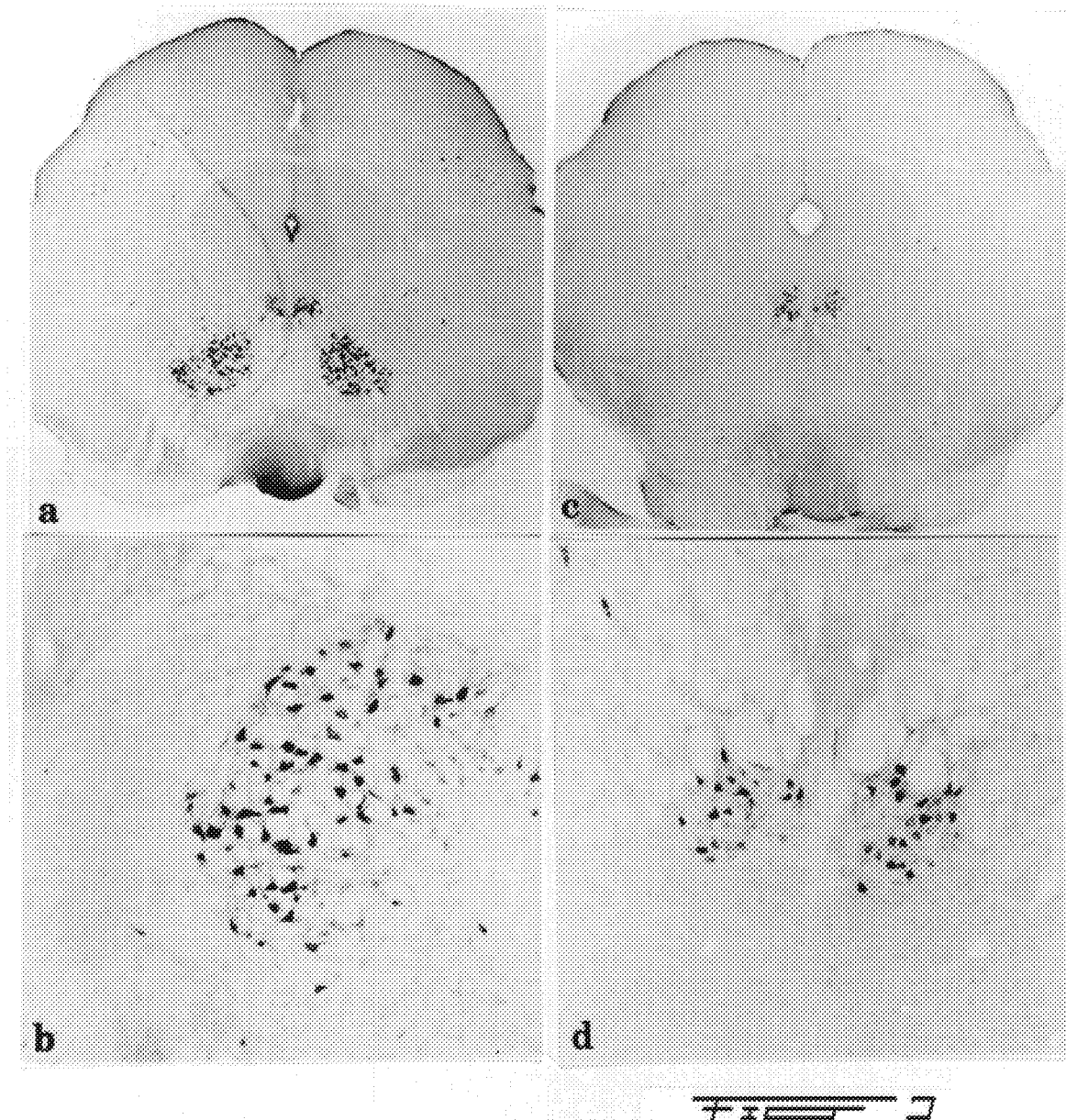

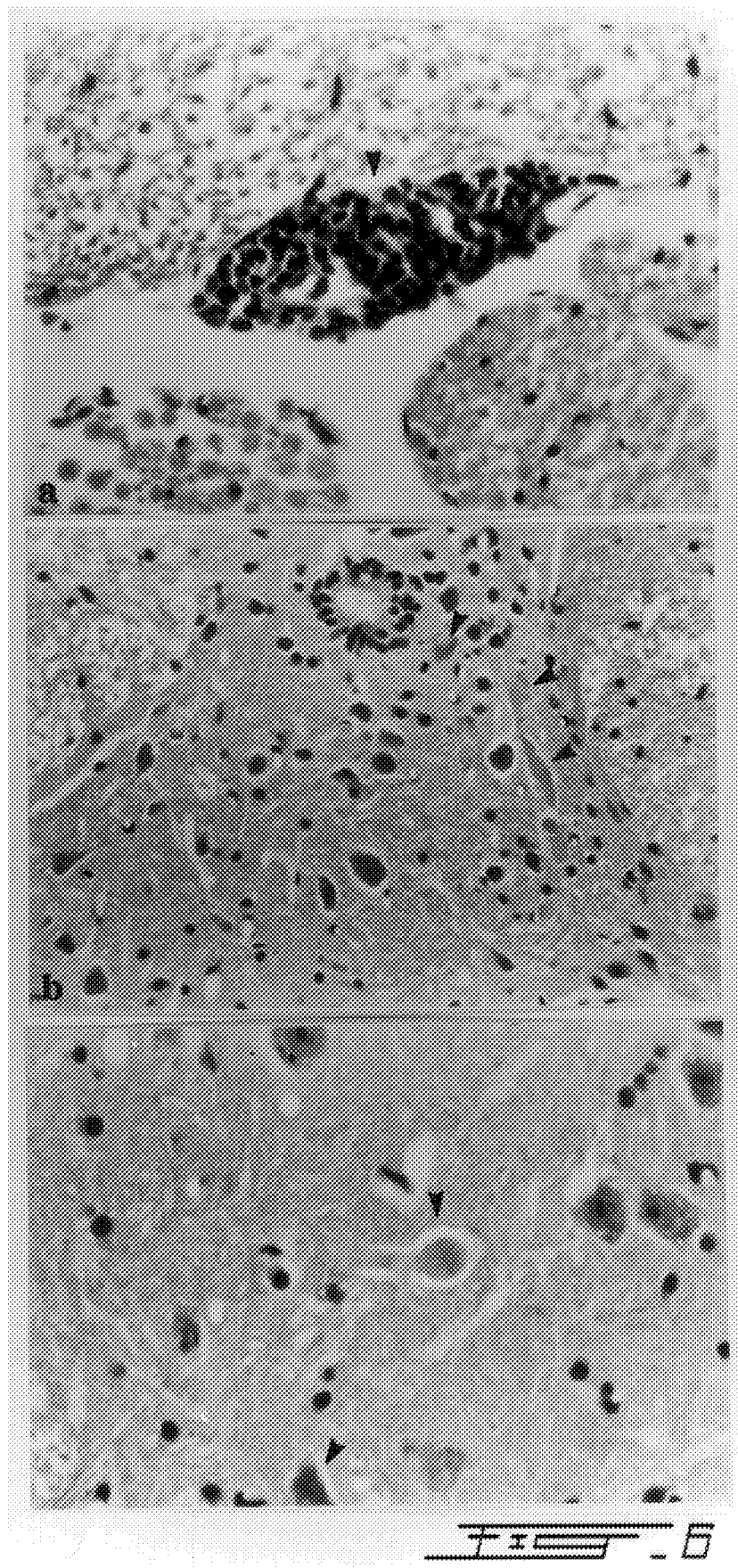

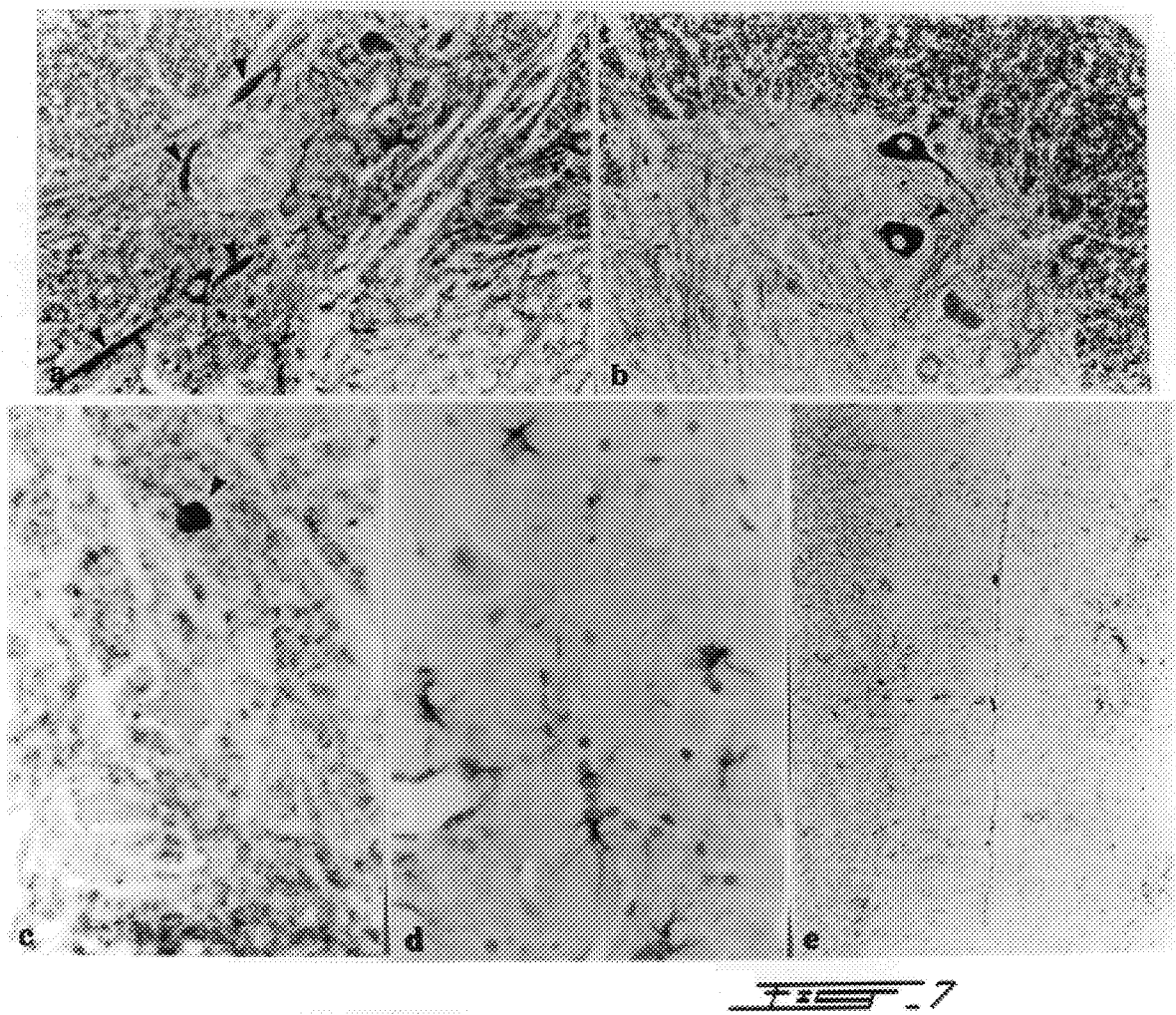

TRANSGENIC MOUSE FOR THE NEURONAL EXPRESSION OF HIV GP160

RELATED APPLICATION

This application is a continuation-in-part of co-pending application No. 08/254,395 filed on Jun. 6, 1994, now U.S. Pat. No. 5,569,827.

BACKGROUND OF THE INVENTION (a) Field of the Invention

The invention relates to a transgenic animal for the neuronal expression of HIV-1 gp160.

(b) Description of Prior Art

Human immunodeficiency virus type 1 (HIV-1) is the causative agent of the acquired immune deficiency syndrome (AIDS). As a member of the lentivirinae subfamily of retroviruses, it is recognized for its ability to target the immune system and the nervous tissue (Navia, B. A. et al., 1986 b), Ann. Neurol., 19:525–535; Navia, B. A. et al., 1986 a), Ann. Neurol., 19:517–524).

A few weeks after the primary infection with HIV-1, a burst of virus replication with a high level of viremia occurs. It is during that phase of infection that the virus likely reaches the central nervous system (CNS) (Price, R. W. et al., 1988, Science, 239:586–592). In most cases it remains clinically silent for highly variable periods of time. Occasionally, it produces an acute meningitis or meningoencephalitis. However, in a large number of AIDS patients (30–40%) the virus entry in the CNS intiates a slowly progressive dementing syndrome termed HIV-1-associated motor/cognitive complex (Janssen, R. S., 1991, Neurology, 778:773–785), which impairs cognitive and motor functions and induces behavorial disorders. At autopsy, up to 96% of these patients show neuropathological changes (Budka, H., 1990 a), In: Chopra J, Jagannathan K, Sawhney IMS (eds) Advances in Neurology. Excerpta Medica, Amsterdam, 193–202; Price, R. W. et al., 1988, Science, 239:586–592; Weis, S. et al., 1993, Acta Neuropathol, 85:185–189) that typically define the HIV-1 encephalopathy (HIVE) or leukoencephalopathy (HIVL) (Villa, G. et al., 1993, J Neur Neurosurgery Psy, 56:878–884; (Weis, S. et al., 1993,Acta Neuropathol, 85:185–189).

HIVE is mainly characterized by brain atrophy and histological changes that include white matter pallor and multiple loosely delimitated inflammatory foci disseminated in the gray and white matter (Navia, B. A. et al., 1986 a), Ann. Neurol., 19:517–524; Weis, S. et al., 1993, Acta Neuropathol, 85:185–189). These foci are composed of microglial cells, a few lymphocytes, reactive astrocytes and very charasteristic multinucleated cells of monocyte/ macrophages origin (Budka, H., 1990 a), In: Chopra J, Jagannathan K, Sawhney IMS (eds) Advances in Neurology. Excerpta Medica, Amsterdam, 193–202; Budka, H., 1990 b ), Acta Neuropathol., 79:611–619; Budka, H. et al., 1991, Brain Patholo., 1:143–152). HIVL is characterized by diffuse myelin loss, gliosis and perivascular infiltration by monocytes and more rarely multinucleated microglia/ macrophages. The deep white matter is preferentially and symmetrically affected (Budka, H., 1990 a), In: Chopra J, Jagannathan K, Sawhney IMS (eds) Advances in Neurology. Excerpta Medica, Amsterdam, 193–202; Budka, H., 1990 b), Acta Neuropathol., 79:611–619; Budka, H. et al., 1991, Brain Patholo., 1:143–152). In HIVE as well as in HIVL, the giant multinucleated cells are considered as the pathological hallmark and in both, morphometric studies have clearly demonstrated a significant neuronal loss (Epstein, L. G. et al., 1986, Pediatrics, 78:678–687; Ketzler, S. et al., 1990, Acta Neuropathol. (Berl), 80:92–94; Masliah, E. et al., 1992, Lab. Investigation, 66:285–291; Weis, S. et al., 1993, Acta Neuropathol, 85:185–189). In addition to these CNS changes, the spinal cord of HIV-1 infected patients may also present alterations such as myelitis or a peculiar vacuolar myelopathy for which no clear etiology has been determined yet.

Several investigators have tried to identify the cells which support the expression and replication of the virus. These studies have demonstrated HIV-1 products in mononucleated and multinucleated macrophages glial cells (Cheng-Mayer, C. et al., 1987, Proc. Natl. Acad. Sci. USA, 84:3526–3530; Epstein, L. G. et al., 1986, Pediatrics, 78:678–687; Gyorkey, F. et al., 1987, J. Infect. Diseases, 155:870–876; Koenig, S. et al., 1986, Science, 233:1089–1093; Stoler, M. H. et al., 1986, JAMA, 256:2360–2364; Vazeux, R. et al., 1987, American J. Pathol., 126:403–410; Wiley, C. A. et al., 1986, Proc. Natl. Acad. Sci. USA, 83:7086–7093) endothelial cells and astrocytes (Epstein, L. G. et al., 1993, Ann. Neurol., 33:429–436; Wiley, C. A. et al., 1986, Proc. Natl. Acad. Sci. USA, 83:7086–7093) microglial cells, but not in neurons (Savio, T. et al., 1993, J. Neurosc. Res., 34:265–272; Sweetnam, P. M. et al., 1993, Eur. J. Neurosc., 5:276–283). Furthermore, HIV-1 has been rescued from brain tissue and cerebrospinal fluid, but not from neurons (Pulliam, L. et al., 1993, AIDS Res Hum Retroviruses, 9:439–444). These findings appear rather paradoxical, considering the cognitive/motor dysfunctions, the dementing illness and the neuronal loss observed in many HIV-1 patients.

In absence of evidence for neuronal infectivity, several direct and indirect mechanisms have been proposed to account for the motor/cognitive disorders. a) It has been postulated that HIV-1 infection of monocytes or macrophages may activate inappropriate secretion of cytokines, such as interleukine-1 or tumor necrosis factor (TNF), that may impair neuronal and/or glial cell function or compromise the integrity of the blood-brain barrier (Wigdahl, B. et al., 1989, AIDS Res. Hum. Retroviruses, 5:369–374). b) Based on experimental observations showing that HIV-1 glycoprotein gp120 could inhibit the growth of neurons in the presence of neuroleukin, but not in the presence of nerve growth factor (Lee, M. R. et al., 1987, Science, 237:1047–1051), it has been suggested that the HIV-1 env protein may bind to and compete for neuroleukin receptors (Brenneman, D. E. et al., 1988, Nature (London), 335:639–642; Lee, M. R. et al., 1987, Science, 237:1047–1051). As a consequence, gp120 could directly interfere with neuronal cell function and/or cause neuronal cell death. c) Recent studies have shown that both native and recombinant gp120, added at very low concentrations to neuronal cultures produce a striking increase in free calcium within the cells and cause cell death within 24 hours, an effect which could be abolished by adding nimodipine (100nM), the dihydropyridine calcium channel antagonist (Dreyer, E. B. et al., 1990, Science, 248:364–367), vasoactive intestinal peptide (Brenneman, D. E. et al., 1988, Nature (London), 335:639–642), anti-gp120 antibodies (Dreyer, E. B. et al., 1990, Science, 248:364–367) or NMDA antagonists (Brenneman, D. E. et al., 1988, Nature (London), 335:639–642; Lipton, S., 1991, Brain Pathology, 1:193–199). The neurotoxicity of gp120 may thus be conferred either through the NMDA receptor, via a second messenger, or directly by calcium channels (Levy, J. A. et al., 1985, Lancet, ii:586–588; Lipton, S. A., 1992, Trends Neurosci., 15:76–80; Sweetnam, P. M. et al., 1993, Eur. J. Neurosc., 5:276–283). Since gp120 shares certain sequence homology with vasoactive intestinal peptide it might also compete for the same binding sites and block this neurotransmission (Lee, M. R. et al., 1987, Science, 237:1047–1051). All these studies carried out in vitro have indicated possible mechanisms by which HIV infection could lead to AIDS dementia. However, many aspects related to AIDS neurophysiopathology are still obscure and could not be approached by in vitro techniques.

It would be highly desirable to be provided with transgenic mice carrying the HIV-1 env gene under the neuron specific promoter of human neurofilament light gene (NFL) (Julien, J. P. et al., 1987, Genes & Development, 1:1085–1095) or the neuron specific promoter of human neurofilament heavy gene (NFH) to further define the role of gp120 in neurotoxicity. Such an animal model could provide some information on the effect(s) of gp120 when expressed in neuronal cells and should help identify the mechanism(s) involved in AIDS clinical syndrome and neuropathology.

It would be highly desirable to be provided with transgenic animals with the neuronal expression of gp120 and preliminary findings of the pathological evaluation.

SUMMARY OF THE INVENTION

One aim of the present invention is to provide a transgenic mice carrying the HIV-1 env gene under the neuron specific promoter of human neurofilament heavy gene (NFH) to further define the role of gp120.

Another aim of the present invention is to provide transgenic animals with the neuronal expression of gp120 and preliminary findings of the pathological evaluation.

In accordance with the present invention there is provided a transgenic non-human mammal, whose germ cells and somatic cells contain a recombinant env gene sequence which is operably linked to a promoter effective for the expression of the gene in the neuronal tissues of the mammal and effective for the simulation of neurological syndromes associated with HIV-1, the gene being introduced into the mammal, or an ancestor of the mammal, at an embryonic stage.

In accordance with the present invention the transgenic non-human mammal is such that transcription of the env gene may be under the control of a promoter sequence, such as a neuron specific promoter of human neurofilament heavy gene (NFH). The promoter can be synthetic or inducible.

In accordance with the present invention the transgenic non-human mammal can be a rodent, such as a mouse.

In accordance with the present invention the following neuroanatomical abbreviations are used: 3, Oculomotor nucleus; 4, Trochlear nucleus; 6, Abducens nucleus; 7, Facial nucleus; 10, Dorsal motor nucleus of vagus; 12, Hypoglossal nucleus; Acs5, Accessory trigeminal nucleus; Acs7, Accessory facial nucleus; Amb, Ambiguus nucleus; DpMe, Deep mesencephalic nucleus; DRG, Dorsal root ganglia; Gi, Gigantocellular reticular nucleus; IC, Inferior colliculus; LH, Lateral hypothalamic area; LM, Lateral mammillary nucleus; LRt, Lateral reticular nucleus; LVe, Lateral vestibular nucleus; MdV, Medullary reticular nucleus, ventral part; Me5, Mesencephalic trigeminal nucleus; Mo5, Motor trigeminal nucleus; PCom, Nucleus of the posterior commissure; PL, Paralemniscal nucleus; PnC, Pontine reticular nucleus, caudal part; PnO, Pontine reticular nucleus, oral part; Pr5, Principal sensory trigeminal nucleus; R, Red nucleus; SC, Superior colliculus; SNR, Substantia nigra, reticular part; Sp5, Spinal trigeminal tract nucleus; SubCA, Subcoeruleus nucleus, alpha part; SuVe, Superior vestibular nucleus; VLL, Ventral nucleus of the lateral lemniscus.

BRIEF DESCRIPTION OF THE DRAWINGS

FIGS. 2A–2D illustrate the immunodetection of HIV-1 env proteins in CNS sections of transgenic mice 1932 with human anti-HIV-1 serum, where 2A–2B) Immunolabeling of red magnocellular (RMC) and red parvocellular (PRC) nuclei, at 200×and 400×magnification, respectively, 2C–2D) Immunolabelling of the oculomotor neurons, at 200 and 400 magnifications, respectively;

FIGS. 6A–6C illustrate the pathological evaluation of the NFHgp160 transgenic mice (line 1932) with HPS staining: 6A) Perivascular inflammation in the leptomeninges of the spinal cord, 6B) Axonal swellings in dorsal spinal cord; 6C) Degenerated neuron and retracted acidophilic neurons; and FIGS. 7A–7E illustrate the immunopathology evaluation of the spinal cord the NFHgp160 transgenic mice, 7A) Immunostaining of the spinal cord with monoclonal antibodies anti- NF neuronal enhancing axonal swellings, 7B) Immunostaining of occasional motor neuron perikaryons with monoclonal antibodies anti- NF axonal, 7C) Immunostaining of a large grain with anti-synaptophysin monoclonal antibody, 7D–7E) Immunostaining with anti-GFAP showing a significant astrogliosis in the anterior gray horns (7D) and in the cortical layers of the cerebellum (7E).

DETAILED DESCRIPTION OF THE INVENTION

1) Recombinant plasmids

The plasmid harboring the transgene NFHgp160 (FIG. 1A) was derived as follows: a 4.8 kb SalI-XbaI fragment comprising the segment encoding the env protein of HXBc2 provirus was deleted from the env expressor plasmid, psvIIIexE7, (kindly provided by Dr. E. Cohen, University of Montreal) and inserted to the 3' end of a 2.4 kb fragment that contains the promoter of the human neurofilament heavy gene (gift of Dr. J. P. Julien). The HXBc2 fragment harbors the coding sequences of env and rev which is required for the transport of env mRNA from the nucleus to the cytoplasm. It also contains non-functional vpu and nef genes (because of a premature stop codon in their respective sequences), the entire 3' LTR that provides the polyadenylation signal and 1.3 kb of cellular sequences. The transgene (7.2 kb) was excized from the pUC18 vector by EcoRI digestion.

Figure 1A:
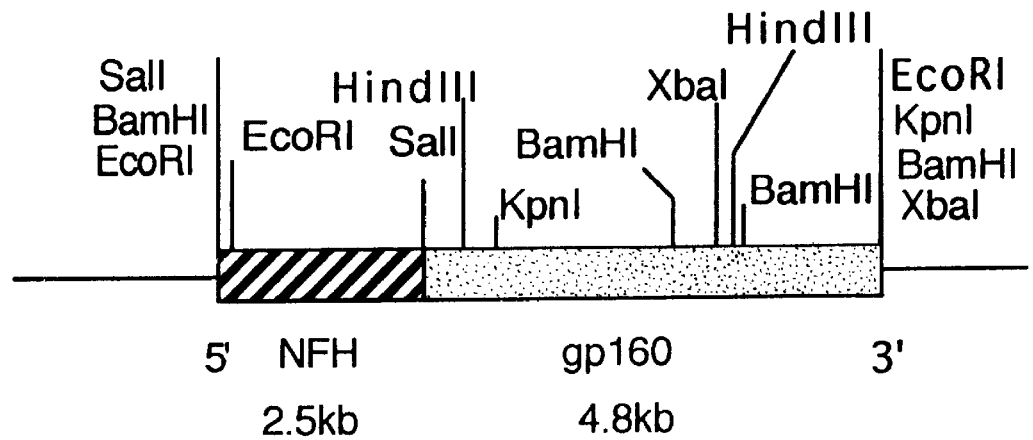
FIGS. 1A–1B illustrate the structure and restriction map of NFHgp160Xba and KS-StyT3 plasmids in accordance with the present invention.

In FIG. 1A, the plasmid Bluscript pSKNFH, harboring the 2.5kb NFH promoter, was modified by introducing a Sal I site at the unique Not I restriction site. The 4.8 kb SalI-XbaI gp160 fragment of HIV-1 HXBc2 strain was introduced in the pUC18 at SalI and XbaI sites as described (Berrada, F. et al., 1995, J. Virol., 69:6770–6778). The 2.5 kb SalI segment containing the human NFH promoter was inserted in SalI site at the 5' end of the HIV-1 4.8 kb fragment. The NFHgp160 transgene was deleted from the vector pUC18 by EcoR I digestion before microinjection.

Figure 1B:
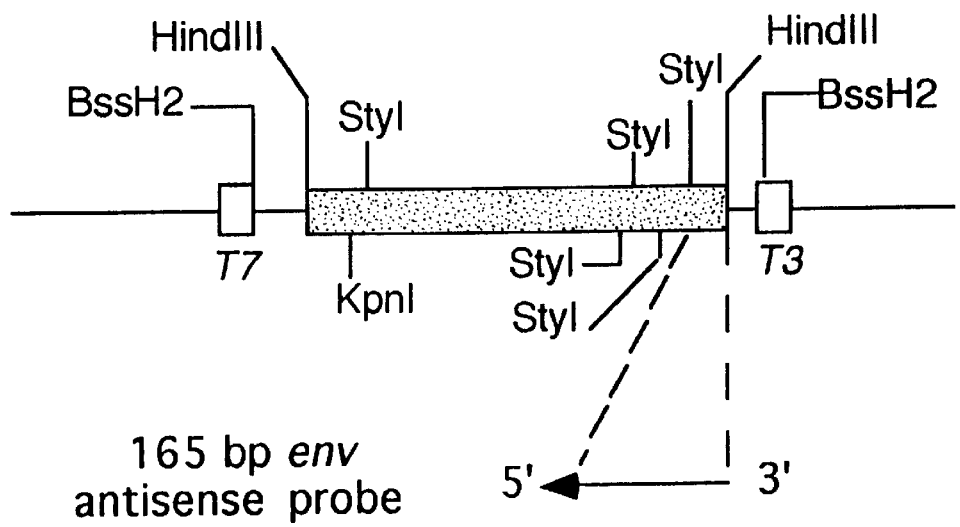

The KS-Sty construct (FIG. 1B) was derived to provide the probes for Southern, Northern and RNase protection analyses. This construct harbors the 2.2kb Hind-III fragment of the env gene in Bluescript KS(+) vector (Stratagene). In FIG. 1B, KS-StyT3 plasmid was constructed by insertion of the 2.2 kb Hind III subfragment of HIV-1 env gene in Hind-III site of Bluescript KS+ vector.

2) Cell cultures and transfections

The cell lines Cos-1, HeLa-CD4+ and HeLa-CD8+ used for transfection experiments were all maintained in Dulbecco modified Eagle medium (DMEM, Gibco/BRL) supplemented with 10% fetal bovine serum (Gibco/BRL.) and 0.1% gentamicin. HIV-1 infected and non-infected U937 were maintained in RPMI (Gibco/BRL) medium supplemented with 10% fetal bovine serum and 0.1% gentamicine. The transfections were performed by the standard calcium phosphate technique as described by (Shen, Y. M. et al., 1982, Mol. Cell. Biol., 2:1145–1154) Fifteen micrograms of plasmid DNA, coprecipitated with calcium phosphate, were added for 12–16 hours to rapidly growing cells plated onto a 10 cm diameter plate containing 10 ml DMEM supplemented with 10% fetal bovine serum and 0.1% gentamicine. The cells were then rinsed with DMEM and incubated in fresh medium for 36 to 48 hours.

3) Immunoreactions a) Immunoprecipitation

The expression of gp160 precursor protein and its processed products, gp120 and gp41, was assessed by immunoprecipitation of Cos-1 cells transfected with the transgene construct. Two days after transfection with either NFLgp160, psvIIIexE7 (positive control) or psvIIIexΔE7 (negative control), Cos-1 cells were labelled with 100 μCi/ml of [$^{35}$S]cysteine (600Ci/mmol) for 6 hours in cysteine-deficient DMEM. HIV-1 infected U937 cells were similarly labelled in cysteine deficient RPMI. The cells were washed and lysed in RIPA lysis buffer (20 mM Tris-HCl [pH 8.0 1], 1 mM EDTA, 120 mM NaCl, 1% NP40, 0.1% sodium dodecyl sulfate [SDS], 0.25% deoxycholate 0.2% phenylmethylsulfonyl fluoride). The cell lysates were first clarified by centrifugation at 13000 rpm for one hour at 4° C. and the supernatant was reacted with normal serum for 2 hours at 4° C. The precipitates were pelleted by centrifugation at the same speed for 5 minutes; the supernatants were incubated at 4° C. overnight with the immunoserum of an HIV-1 infected patient. The immune complexes were precipitated for 2 hours at 4° C. with 50 μl of protein A-sepharose suspension. The precipitates were finally pelleted, washed 6 times with 1 ml of washing buffer (1% NP40, 120 mM NaCl, 20 mM Tris-HCl, pH 8.0) and resuspended in 50 μl of 2×SDS gel loading buffer (100 mM Tris.-HCl, pH 6.8, 200 mM dithiothreitol, 0.4% SDS, 0.2% bromophenol blue and 20% glycerol). They were boiled for 3 minutes and fractionated on a 9% polyacrylamide/SDS gel. The gels were dried and exposed to radioautographic films for 24 to 48 hours.

b) Immunoperoxidase staining

For immunoperoxidase reaction, Cos-1, HeLa-CD4+ and HeLa-CD8+ cells were seeded on glass coverslips and transfected as described above. Forty-eight hours later, the transfected cells and the appropriate controls were rinsed with PBS, air dried, fixed in cold acetone for 10 minutes and reacted first with a normal serum for 20 minutes and then with mouse monoclonal antibodies (Dupont/NEN) directed against gp41 or gp120. The immunoreactivity was revealed according to the avidin/biotin/peroxidase method (ABC) using a biotinylated horse anti-mouse IgG and an ABC complex (Vectastain, Vector) with diaminobenzidine as chromogen. The cells were then rinsed with PBS, stained with hematoxylin for 10 seconds, washed in water, dehydrated in ethanol and coverslipped with DPX.

4) Microinjection of fertilized mouse eggs

The 10.5 kb fragment containing the transgene NFLgp160Xba was deleted from the plasmid using NotI enzyme (FIG. 1A), purified with several phenol/chloroform extractions and ethanol precipitation and finally microinjected at 2 μg/ml into the male pronuclei of fertilized eggs. Microinjected eggs were transferred to the oviducts of pseudopregnant females. All the transgenic mice were developed and maintained in a pathogen-free facility.

5) DNA analysis of transgenic mice

The integration of the transgene into the mouse genome was assessed by Southern blot hybridization of genomic DNA. Tail samples of 3 week old mice were digested with proteinase K at 55° C. for at least 5 hours and the DNAs were purified by several phenol/chloroform/isoamyl alcohol and chloroform extractions followed by ethanol precipitation. Ten to 15 μg genomic DNAs were digested with either Sac-l or EcoR-l enzymes, fractionated on 1% agarose gels and transferred to nitrocellulose membrane (Schleicher & Schuell). The filters were prehybridized in 5×SSC (1 SSC is 150 mM NaCl and 5 mM Na$_3$ citrate [pH 7]) 1% SDS, 20 mM Tris (pH 7.5), 5×Denhart's solution (1×Denhart is 0.02% bovine serum albumine, 0.02% Ficoll™, 0.02% polyvinyl pyrolidone), 10% dextran sulfate and 100 μg/ml denatured salmon sperm DNA for at least 3 hr at 65° C. The DNA probe made of the env 2.2kb HindIII subfragment labeled with [a$^{32}$p]dCTP (3000Ci/mmol.) was denatured and added to the filter for an overnight hybridization at 65° C. The filter was then washed 10 min. at room temperature in 2×SSC, 1% SDS; 2×30min. at 65° C. in 1×SSC and 1% SDS; 30 min. in 0.5×SSC,1% SDS; 1 min. in 0.2×SSC at room temperature. The filters were finally exposed to Kodak™ X-Omat AR and/or RP with an intensifying screen.

6) Transgenic mice

The integration of the transgene in the mouse genome was determined by Southern blot hybridization of genomic DNA extracted from mice tails.

With the NFHgp160 transgene, 5 founders which tested positive for the presence of the transgene were obtained. One of these founders (No. 1932) has been fully investigated for the neuronal expression of the HIV-1 Env proteins and their distribution in the CNS, as well as for the pathological alterations induced by these proteins.

7) Expression and distribution of the Env protein in the transgenic mice 1932

This was determined by immunohistochemistry, using the same antibodies and reaction conditions as previously described (Berrada, F. et al., 1995, *J. Virol.*, 69:6770–6778). As in the NFLgp160Xba transgenic mice, the NFHgp160 mice (line 1932) demonstrated the neuronal expression of the Env proteins in several structures of the mesencephalon, the pons, the medulla and the spinal chord. In addition, they also showed expression of the transgenic proteins in cerebellar structures that always tested negatively in NFLgp160Xba mice.

Figure 3:
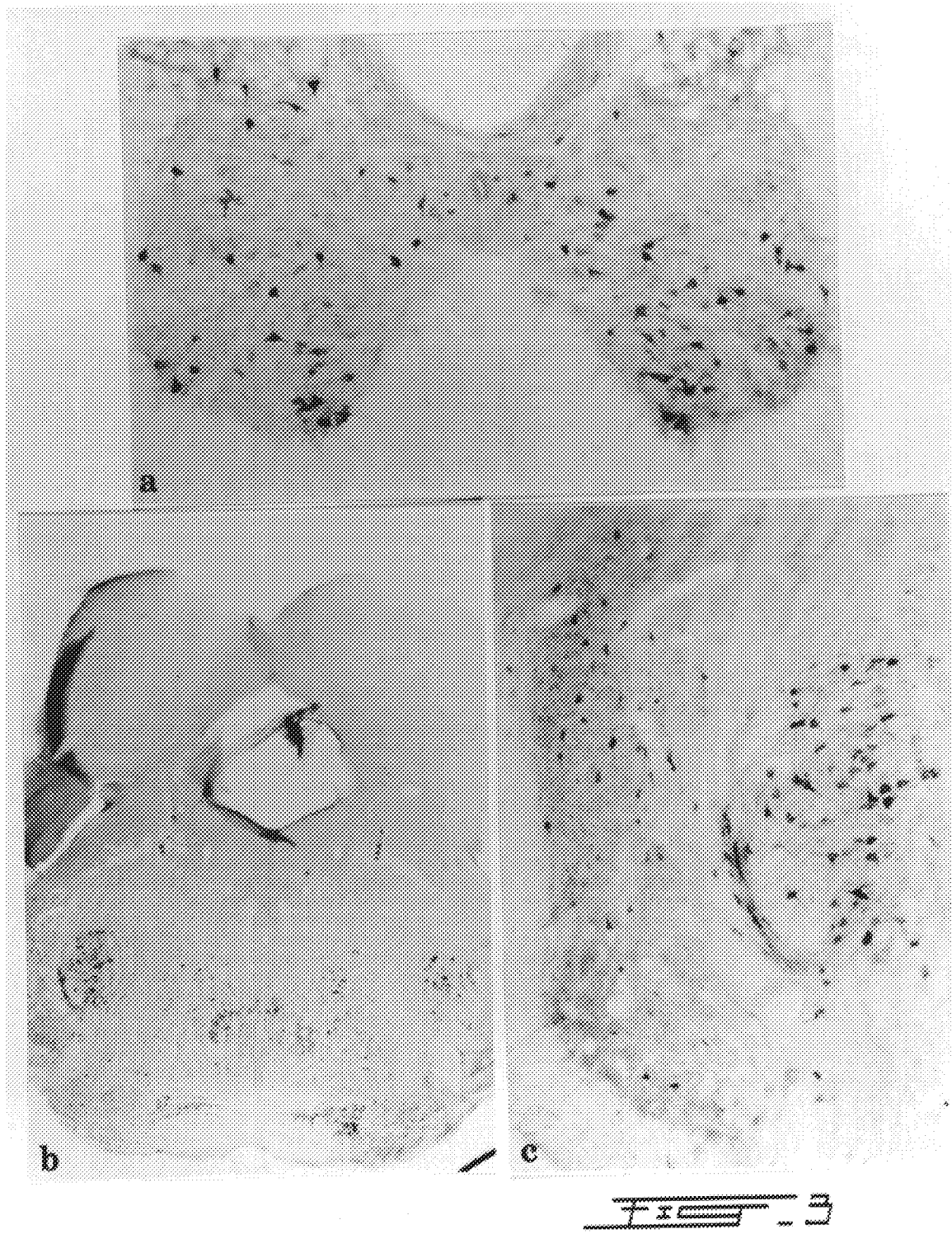
FIGS. 3A–3C illustrate the immunodetection of HIV-1 env proteins in CNS sections of transgenic mice 1932 with human anti-HIV-1 serum, where 3A) Immunostaining of neurons in the anterior gray horns of the spinal cord, 400×, 3B–3C) Immunostaining of the motor trigeminal (Mo5) and principal sensory trigeminal nuclei, at 200×and 400× magnifications, respectively.
Figure 4:
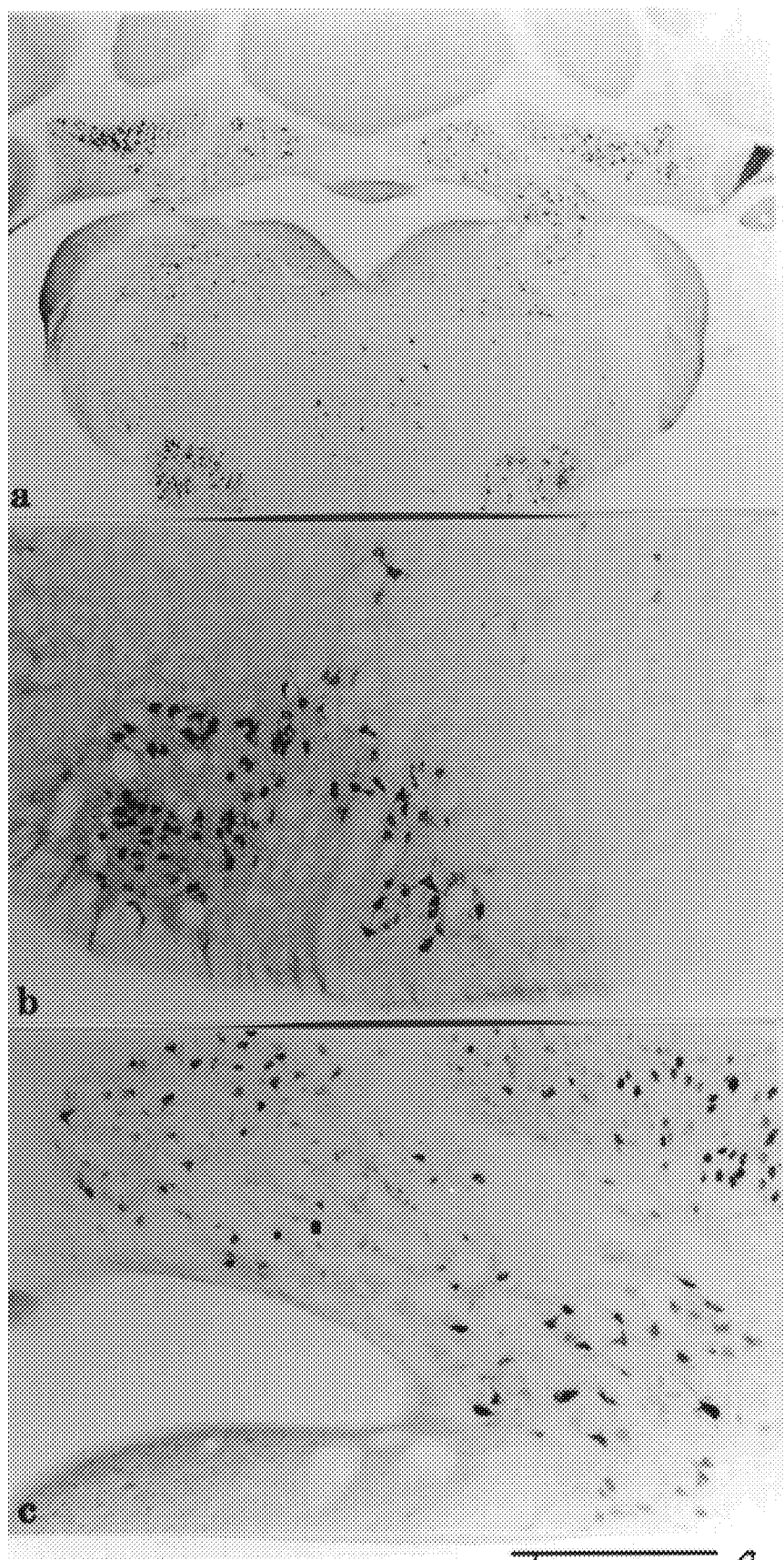
FIGS. 4A–4C illustrate the immunodetection of HIV-1 env proteins in CNS sections of transgenic mice 1932 with human anti-HIV-1 serum, where 4A and 4C) Immunostaining of cerebellar structures, at 200×and 400×magnification, respectively, 4A and 4B) Immunostaining of the facial nuclei at 200×and 400×magnifications, respectively.
Figure 5A:
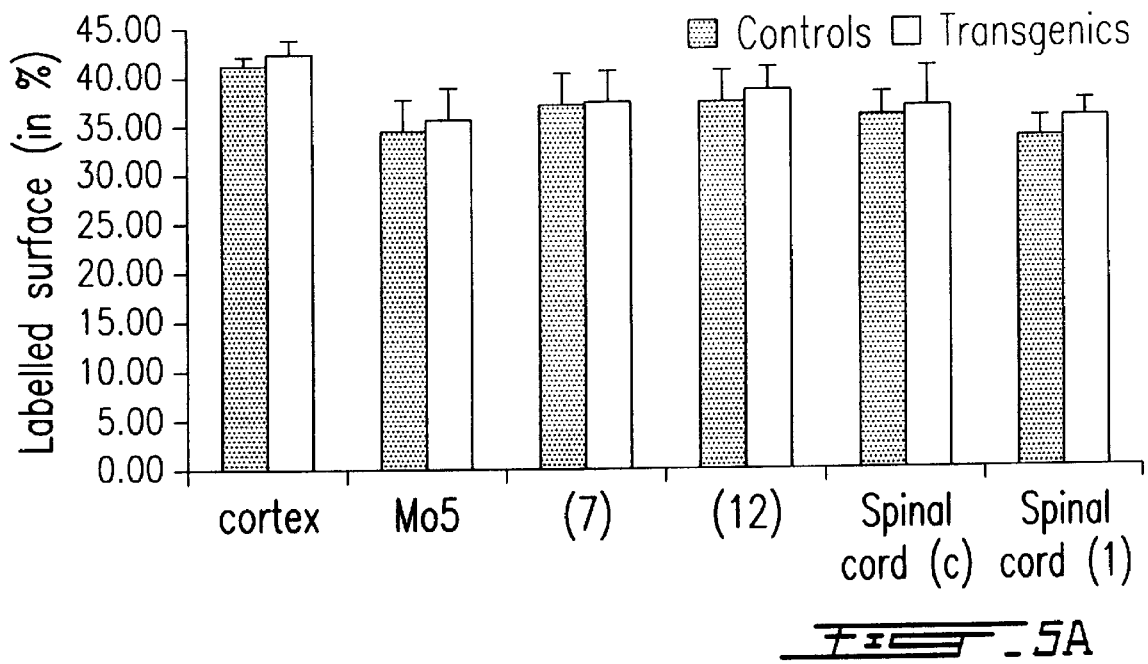
FIG. 5 illustrates the confocal microscopy evalution of the MAP-2 and GFAP in the cortex, the motor trigeminal (Mo5), facial (7) and hypoglossal (12) nuclei and in the anterior gray horns of the spinal cord of control and transgenic mice.
Figure 5B:
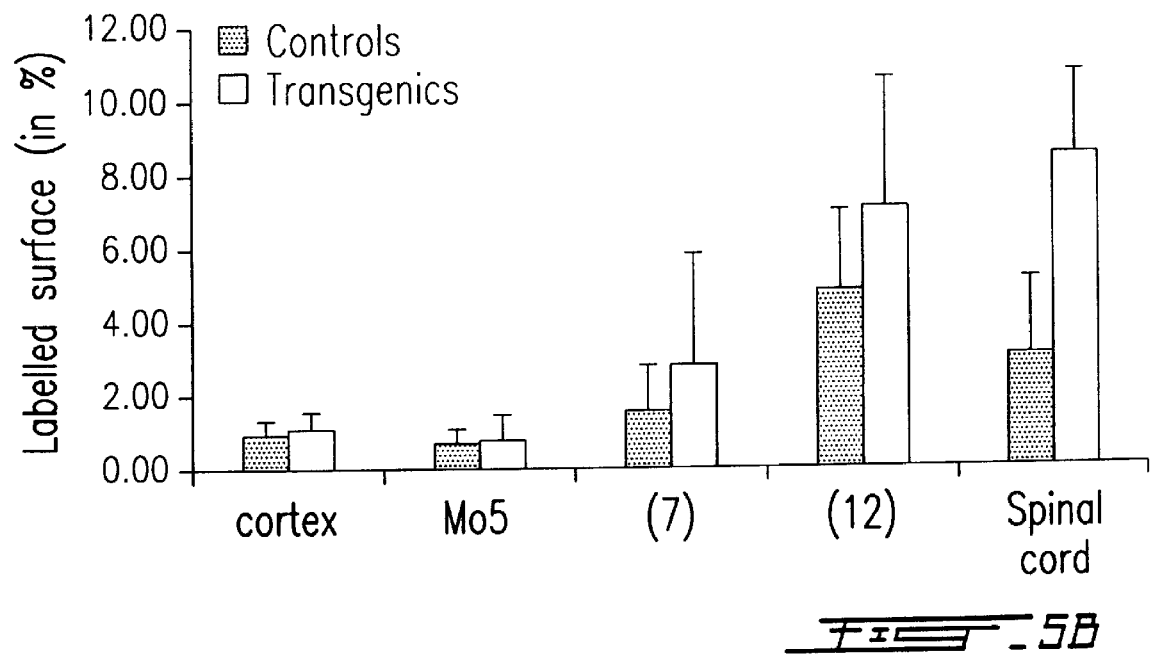

The distribution of the Env proteins in the NFHgp160 (line 1932) mice was as follows:

Mesencephalon
  Oculomotor (3), ventral pallidum (VP), medial longitudinal fasciculus (mlf), red magnocellular nuclei (RMC), red parvocellular nuclei (RPC) (FIGS. 2A, 2B, 2C, 2D).
Pons
  Motor trigeminal nuclei (5) (FIGS. 3B, 3C), facial nuclei 7 (7) (FIG. 4B), principal sensory trigeminal nucleus (Pr5) (FIG. 3C), spinal vestibular nuclei (SpVe), medial vestibular nuclei (MVe), lateral vestibular nuclei (LVe), pontine reticular nuclei (PnC/V), reticulo tegmental nuclei pons (RtTg), dorsal paragigantocellular nuclei (DPGi), nucleus Y (Y), ventral cochlear nuclei anterior (VCA).
Medulla
  Hypoglossal nuclei (12), gigantocellular reticular nuclei (GiA, GiV), solitary tract (sol), rostroventrolateral reticular nuclei (RLV), lateral reticular nuclei (LRt), cuneate fascicles (cu), prepositus hypoglossal nuclei (PrH), trapezoid body (tz), linear nuclei of medulla (Li), medullary reticular nuclei ventral (MdV).
Cerebellum
  Interposed cerebellar nuclei anterior (Int A), medial cerebellar nuclei (Med DL), lateral cerebellar nuclei (Lat PC) (FIGS. 4A, 4C)
Spinal cord
  DRG, motoneurons in layers 5–9 (FIG. 3A).
  Thus, in the transgenic 1932 animals, the expression of the HIV-1 Env proteins was found extended to additional structures of the pons and to the cerebellum.

8) Pathological alterations

The morphological alterations of the NFLgp160Xba transgenic mice (lines 844 and 854) were previously described (Berrada, F. et al., 1995, *J. Virol.*, 69:6770–6778). Further immunohistochemical studies were performed using the following antibodies: phosphorylated axonal neurofilament (NF-a), nonphosphorylated neuronal neurofilament (NF-n), neuronal specific enolase (NSE), synaptophysin (Sy) and tubulin. NF-a enhanced the dendritic swellings that have been observed with the anti-gp160 antibodies (Berrada, F. et al., 1995, *J. Virol.*, 69:6770–6778). The reactions with the NF-a, NF-n, NSE and tubulin suggested a slight enhancement of the density of dendritic projections in the neuropil of the anterior horns. In the anterior horns of the spinal cord, Sy showed grain irregularities when compared to controls; there were also occasional aggregates of larger grains which signal a disturbance in distribution and/or size of the synapses. Morphometric studies with confocal microscopy using glial fibrillary acidic protein (GFAP), microtubule-associated protein 2 (MAP-2) and Sy were done on the anterior horns of the spinal cord, the hypoglossal (12), facial (5) and trigeminal motor (Mo5) nuclei. These studies confirmed a significant gliosis in the anterior horns with the GFAP (FIG. 6). The gliosis is increased in the motor nuclei of the brainstem but it is not statistically significant. With the MAP-2 (FIG. 6) and Sy, there is a slight increase, although statistically not significant, of both reactions in the transgenic animals.

The NFHgp160 transgenic mice (line 1932) were similarly investigated at the age of 12 months. With HPS staining, a chronic perivascular inflammation was observed in the leptomeninges of the spinal cord and brainstem and, also, in the white matter of the cerebellum (FIG. 6A). Lymphocytes were present in the infiltrate. In the anterior horns of the spinal cord, there was a neuronal loss along with a few degenerated neurons (FIG. 6C) and retracted acidophilic neurons. A moderate astrocytosis was found associated with these changes. In addition, in these areas as well as in the dorsal and posterior and anterior funiculi, dendritic and axonal swellings and acidophilic deposits were observed (FIG. 6B). The swellings were best seen immunohistochemically with the NF-n antibodies (FIG. 7A). In the brainstem and in the cerebellum, a moderate gliosis (FIG. 7D) was also noted. It was particularly striking in the cortical layers of the cerebellum. (FIG. 7E)

As in the NFLgp160Xba mice, the immunohistochemical reactions with NF-n, NF-a, NSE and synaptophysine enhanced the projections in the neuropil of the anterior horns comparatively to the control mice (FIGS. 7A, 7B, & 7C). Here again, Sy showed grain irregularities when compared to controls; occasional aggregates of larger size were observed (FIG. 7C) In addition, the NF-a, which is specific for the axonal neurofilament, stained the perikaryons of a significant number of neurons in the anterior horns of the spinal cord and in some cranial nerve nuclei. (FIG. 7B)

Thus, the NFHgp160 transgenic mice (line 1932) demonstrated not only the changes already described in the NFLgp160Xba mice but also additional pathological modifications including the perivascular inflammation in the leptomeninge, the neuronal expression of gp160 in certain cerebellar structures and a positive reaction with NF-a in the perikaryons.

Further studies using offsprings obtained from matings of different transgenic lines will help determine the effects of higher levels of gp120 on CNS morphology. In addition, the neuronal expression of env proteins at levels detectable by immunocytochemistry in several CNS regions of these animals provides useful models for studies of the neuropathological effects of gp120 during embryonic development and ageing.

Uses of the transgenic mice

The transgenic mice of the present invention can be used for the study of neurobiology and to understand the function of neuronal cells.

The transgenic mice of the present invention can be used for the study of the mechanism of the neurotoxicity induced by gp160.

The transgenic mice of the present invention can be used to test pharmaceutical compounds for used as antagonist against the neurotoxicity induced by gp160 or for the treatment of the neuronal syndrome of HIV-1 infections.

The transgenic mice of the present invention can be combined to other transgenic mice which are carrying other genes of HIV for the study of the pathogenesis of this virus and the testing of pharmaceutical compounds effective against the pathogenesis.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

Other embodiments are within the following claims. For example, any species of transgenic animal can be employed. In some circumstances, for instance, it may be desirable to use a species, e.g., such as the rhesus monkey, which is evolutionary closer to human.

We claim:

1. A transgenic mouse, whose germ cells and somatic cells contain a recombinant env gene sequence which is operably linked to a neuron specific promoter of human neurofilament heavy gene (NFH) effective for the expression of said gene in the neuronal tissues of said mouse and effective for the simulation of neuropathological changes associated with HIV-1 selected from the group consisting of HIV-1 immunoreactive axonal swelling, dendritic swellings, astrocytosis in the central nervous system, said gene being introduced into said mouse, or an ancestor of said mouse, at an embryonic stage.

* * * * *